(12) United States Patent
Kinney et al.

(10) Patent No.: US 6,933,383 B2
(45) Date of Patent: Aug. 23, 2005

(54) REGIOSELECTIVE AND STEREOSELECTIVE OXIDATION OF FUSED RING SYSTEMS USEFUL FOR THE PREPARATION OF AMINOSTEROLS

(75) Inventors: William A. Kinney, Newtown, PA (US); Xuehai Zhang, East Norriton, PA (US); Ronald Michalak, Congers, NY (US)

(73) Assignee: Genaera Corporation, Plymouth Meeting, PA (US)

( * ) Notice: Subject to any disclaimer, the term of this patent is extended or adjusted under 35 U.S.C. 154(b) by 0 days.

(21) Appl. No.: 10/268,660

(22) Filed: Oct. 11, 2002

(65) Prior Publication Data

US 2003/0171576 A1 Sep. 11, 2003

Related U.S. Application Data

(63) Continuation of application No. PCT/US01/12004, filed on Apr. 12, 2001.
(60) Provisional application No. 60/196,646, filed on Apr. 12, 2000.

(51) Int. Cl.[7] ............................................... C07J 71/00
(52) U.S. Cl. ........................................................ 540/16
(58) Field of Search ........................... 552/553; 540/16

(56) References Cited

U.S. PATENT DOCUMENTS

| | | | |
|---|---|---|---|
| 3,016,390 A | | 1/1962 | Counsell |
| 3,370,070 A | | 2/1968 | Klimstra et al. |
| 4,220,598 A | | 9/1980 | Hixson, Jr. et al. |
| 4,230,625 A | * | 10/1980 | Despreaux et al. ......... 552/551 |
| 4,301,246 A | * | 11/1981 | Despreaux et al. ........... 435/58 |
| 4,372,888 A | | 2/1983 | Hjelmeland |
| 4,425,273 A | | 1/1984 | Iida et al. |
| 4,514,393 A | | 4/1985 | Castagnola et al. |
| 4,545,938 A | | 10/1985 | Mosbach et al. |
| 4,550,163 A | | 10/1985 | Voss et al. |
| 4,565,811 A | | 1/1986 | Di Schiena |
| 4,771,042 A | | 9/1988 | Braughler et al. |
| 4,793,948 A | | 12/1988 | Hatono et al. |
| 4,966,897 A | | 10/1990 | Angelastro et al. |
| 4,994,443 A | | 2/1991 | Folkman et al. |
| 5,001,116 A | | 3/1991 | Folkman et al. |
| 5,004,737 A | | 4/1991 | Kim et al. |
| 5,039,529 A | | 8/1991 | Bergendal et al. |
| 5,057,509 A | | 10/1991 | Pellicciari et al. |
| 5,061,701 A | | 10/1991 | Pellicciari et al. |
| 5,063,222 A | | 11/1991 | Komoto et al. |
| 5,075,464 A | | 12/1991 | Blohm et al. |
| 5,135,919 A | | 8/1992 | Folkman et al. |
| 5,192,756 A | | 3/1993 | Zasloff et al. |
| 5,247,104 A | | 9/1993 | DeLuca et al. |
| 5,250,524 A | | 10/1993 | Kramer et al. |
| 5,637,691 A | | 6/1997 | Frye et al. |

FOREIGN PATENT DOCUMENTS

| | | |
|---|---|---|
| EP | 0 018 515 A | 11/1980 |
| EP | 0 394 971 A1 | 10/1990 |
| EP | 0 466 315 A2 | 1/1992 |
| FR | 2 361 899 | 3/1978 |
| GB | 1 565 351 | 4/1980 |
| WO | 87/02367 | 4/1987 |
| WO | 91/19731 | 12/1991 |
| WO | 93/25197 | 12/1993 |
| WO | 94/17079 A | 8/1994 |
| WO | 94/19366 | 9/1994 |
| WO | 94/20520 | 9/1994 |
| WO | 94/24800 A | 10/1994 |
| WO | 95/24415 | 9/1995 |
| WO | 96/40151 | 12/1996 |
| WO | 96/40728 | 12/1996 |
| WO | WO 98/24800 | * 6/1998 |

OTHER PUBLICATIONS

Despreaux et al., "Microbial 7alpha–Hydroxylation of 3–Ketobisnorcholenol.", Applied and Environmental Microbiology, vol. 51(5), pp. 946–949, 1986.*
International Search Report of PCT/US 97/22031.
International Search Report of PCT/US 01/12004.
McKenna, et al., "Bis–steroids as Potential Enzyme Models: Perylene Solubilisation and Dye Spectral Changes with Aqueous Solutions of Some Derivatives of Conessine and Cholic Acid:" J.C.S. Chem. Comm., 1977, pp. 809–811.
Crum et al., "A New Class Steroids Inhibits Angiogenesis in the Presence of Heparin a Heparin Fragment", Science, vol. 230, 1985, pp. 1375–1378.
Derwen Abstract No. 86–085704, Anticancer Drug Contains Shark Liver Extract Doxorubicin, 1984.
Biosis No. 82085007, "Studies on Antitumor Activity of Squalene and Its Related Compounds", Yakugaku Zasshi, 1986.
Chemical Abstract No. 111: 17264, "Increasing the Therapeutic Efficacy of Antitumor Drugs", 1989.
Bellini et al., "Antimicrobial Activity of Basic Cholane Derivatives, Part IX," Arch, Pharm. (Weinheim), vol. 323, pp. 201, 205, (1990).
Nath, "The Novel Aminosterol Antibiotics Squalamine and 1436 are Specific Inhibitors of Epithelial Brush Border $Na^+/H^{30}$ Exchanger (NHE) Isoform, NHE3", Gastroenterology, vol. 110, No. 4, Suppl. (1996), A349.

(Continued)

Primary Examiner—Barbara P. Badio
(74) Attorney, Agent, or Firm—Morgan, Lewis & Bockius LLP (57) ABSTRACT

An efficient method for the synthesis of aminosterol compounds such as squalamine and compound 1436 is described. A method of the invention provides for regioselective oxidation and regioselective sulfonation of a fused ring system. The fused ring base can be, for example, a steroid ring base. The aminosterol compounds are effective as, for example, antibiotics, antiangiogenic agents and NHE3 inhibitors.

4 Claims, 2 Drawing Sheets

OTHER PUBLICATIONS

Bellini et al., Antimicrobial Activity of Basic Cholane Derivatives. X. Synthesis of 3α–and 3β–amino–5β–cholan–24–oic Acids, *Steroids*, vol. 56, Jul. 1991, pp. 395–397.

Gagliardi et al., "Inhibition of Angiogensis by Antiestroens," *Cancer Research*, vol. 53, pp. 533–535, (1993).

Moore et al., "Squalamine: An Aminosterol Antibiotic from the Shark," *Proc. Natl. Acad. Sci., USA*, vol. 90, pp. 1354–1358, (1993).

Wehrli, et al., "Structure of the Novel Steroidal Antibiotic Squalamine Determined by Two Dimensional NMR Spectroscopy," *Steroids*, vol. 58, No. 8, (1993), pp. 370–378.

Auerbach et al., "Angiogenesis Inhibition: A Review", *Pharmac. Ther.*, vol. 63, pp. 265–320 (1994).

Moriarty et al., "Synthesis of Squalamine, A Steroidal Antibiotic from the Shark", *Tetrahedron Letters*, vol. 35, No. 44, pp. 8103–8106, (1994).

Sadownik et al., "Rapid Construction of a Squalamine Mimic", *J. Am. Chem. Soc.*, (1995), vol. 117, pp. 6138–6139.

"Designing Therapies that Target Tumor Blood Vessels," *Science*, vol. 275, (1997), pp. 482–484.

Akhter, "Squalamine, A Novel Aminosterol Antibiotic is a Specific Inhibitor of Epithelial Border $Na^+/H^+$ Exchanger (NHE) Isoform, NHE3," *Gastroenterology*, vol. 110, No. 4, Suppl. (1996), A349.

Larock, *Comprehensive Organic Transformations, A Guide to Functional Group Preparations*, pp. 421–428 (1989).

Richer et al., "Equilibration D'imines clyclaniques," *Can. J. Chem.* vol. 48, pp. 3412–3422 (1983).

Layer, "The Chemistry of Imines," *Chem. Rev.*, 63, pp. 489–510 (1993).

Hutchins et al., "Stereoselective Reductions of Substituted Cyclohexyl and Cyclopentyl Carbon–Nitrogen pi Systems with Hydride Reagents," *J. Org. Chem.* vol. 48, pp. 3412–3422 (1983).

Kyba et al., "Primary Alkyl Amines. Generation by Reduction of α–Alkoxyazides," *Tetrahedron Letters*, No. 32, pp. 2737–2740, (1977).

Borch, et al., "Lithium Cyanohydridoborate," *J. Am. Chem. Soc.*, vol. 91, No. 14, pp. 3996–3997, (1969).

Yamamoto et al., "Regioselective Carbonyl Amination Using Diisobutylaluminum Hydride," *J. Am. Chem. Soc.*, vol. 103, pp. 4186–4194, (1981).

Tadanier et al., "6'–epi–Fortimicins," *Tetrahedron*, vol. 37, pp. 1309–1316, (1981).

E. J. Corey et al., "A Stable and Easily Prepared Catalysts for the Emantioselective Reduction of Ketones. Applications to Multistep Syntehesis", *J. Am. Chem. Soc.*, vol. 109, pp. 7925–7926, (1987).

Parker et al., "Asymetric Reduction. A Convenient Method for the Reduction of Alkynyl Ketones", *J. Org. Chem.*, vol. 61, pp. 3214–3217, (1996).

Wallbaum et al., "Asymmetric Syntheses with Chiral Oxazaborolidines", *Tetrahedron: Asymmetry*, vol. 3, No. 12, pp. 1475–1504, (1992).

Okamoto et al., "Asymmetric Isopropylation of Steroidal 24–Aldehydes for the Synthesis of 24(R)–Hydroxycholesterol", *Tetrahedron: Asymmetry*, vol. 6, No. 3, pp. 767–778 (1995).

Okamoto et al., "The First Convergent Synthesis of 1.alpha, 24 (R)–Dihydroxyvitamin D3 via Diastereoselective Isopropylation and Alkylative Enyne Cyclization", *Tetrahedron*, vol. 51, No. 19, (1995), pp. 5543–5556.

Takatsuto et al., "Chirality Transfer in the Cholesterol Side Chain; Synthesis of (24R)– and 24(S)–24–Hydroxycholesterols", *J. Chem. Soc., Chem. Comm.*, No. 4, (1982), pp. 258–260.

Brown et al., "Selective Reductions. 40. A Critical Examination of the Relative Effectiveness of Various Reducing Agents for the Asymmetric Reduction of Different Classes of Ketones", *J. Org. Chem.*, vol. 52, No. 24, (1987), pp. 5406–5412.

Ishiguro et al., "Neighbouring Group Effects. Part 2, Effect of Epoxide on the Hydrolysis of Adjacent Acetate Groups", *J. Chem. Soc., Perkin Transactions 1*, No. 11, (1980), pp. 2507–2510.

Katsumi et al., "Synthesis of 24,25–Dihydroxyvitamin D2, 24,25–Dihydroxy–22–dehydrovitamin D3, 25–Hydroxy–24–oxo–22–dehydrovitamin D3 and 22,24, 25–Trihydroxyvitamin D3", *Chem. and Pharm. Bulletin*, vol. 35, No. 3, (1987), pp. 970–979.

Helal et al., "Direct Catalytic Enantioselective Reduction of Achiral.alpha.,.beta.–Ynones. Strong Remote Steric Effects Across the C–C Triple Bond", *J. Am. Chem. Soc.*: vol. 118, No. 44, (1996).

Imai et al., "Organoboron Compounds in Organic Synthesis. 2. Asymmetric Reduction of Dialkyl Ketones With (R,R)– or (S,S)–2,5–dimethylborolane", *J. Am.Chem.*, vol. 108, No. 23, pp. 7402–7404, (1986).

Bach et al., "High Enantioenriched Propargylic Aclohols by Oxazaborolidine–Mediated Reduction of Acetylenic Ketones", *J. Org. Chem.*, vol. 61, No. 25, pp. 9021–9025, (1996).

Rao et al., "Practical Approaches to Remote Asymmetric Induction in Steroidal Side–Chains Utilizing Oxazaborolidine Reagents", *J. Org. Chem.*, vol. 62, No. 13, pp. 4541–4545, (1997).

Despreaux. et al., "Microbial 7.alpha.–hydroxylation of 3–ketobisnorcholenol", *Appl. Environ. Microbiol.* (1986), vol. 51, No. 5, pp. 946–949.

Zhang et al., "Synthesis of Squalamine Utilizing a Readliy Accessible Spermidine Equivalent" *J. of Org. Chem.*, vol. 63, No. 23, (1998), pp. 8599–8603.

Jones et al., "Efficient Route to 7.alpha.–(Benzoyloxy)–3–dioxolane Cholestan–24(R)–01, a Key Intermediate in the Synthesis of Squalamine", *J. of Org. Chem.*, vol. 63, No. 11, (1998), pp. 3786–3789.

Weis et al., "Synthesis of an Azido Spermidine Equivalent", *Tetrahedron Letters, Elsevier Science Pub.*, vol. 40, No. 26, (1999), pp. 4863–4864.

Pechulis et al., "Synthesis of 23XL–Squalamine, An Anti–Infective Steroidal Polyamine", *J. of Organic Chem.*, vol. 60, No. 16, (1995), pp. 5121–5126.

Maione et al., "Carbonyl Compounds by Osmium Tetroxide Oxidation: Preferential Oxidation of Primary Over Secondary Hydroxy Groups", *Synthesis*, No. 11, (1984), pp. 955–957.

Kinney et al., "A Short Formal Synthesis of Squalamine From a Microbial Metabolite", *Org. Lett.*, vol. 2, No. 19, (2000), pp. 2921–2922.

* cited by examiner

REGIOSELECTIVE AND STEREOSELECTIVE OXIDATION OF FUSED RING SYSTEMS USEFUL FOR THE PREPARATION OF AMINOSTEROLS

This application is a continuation of PCT/US01/12004 filed on Apr. 12, 2001, which claims priority to Provisional Application No. 60/196,646, filed Apr. 12, 2000.

GOVERNMENT FUNDING

The research described in this patent application was funded in part by Small Business Innovative Research Grant #1 R43 CA 80473-01 from the National Cancer Institute of the National Institutes of Health.

BACKGROUND OF THE INVENTION

1. Field of the Invention

The invention relates to a novel method of producing fused ring based compounds or aromatics including aminosterol compounds. A method of the invention offers regioselective oxidation and regioselective sulfonation of fused ring systems with few protecting groups. The aminosterol compounds produced by a method of the invention are useful as, among others, antibiotics, antiangiogenic agents and NHE3 inhibitors.

2. Description of the Related Art

Figure 1:
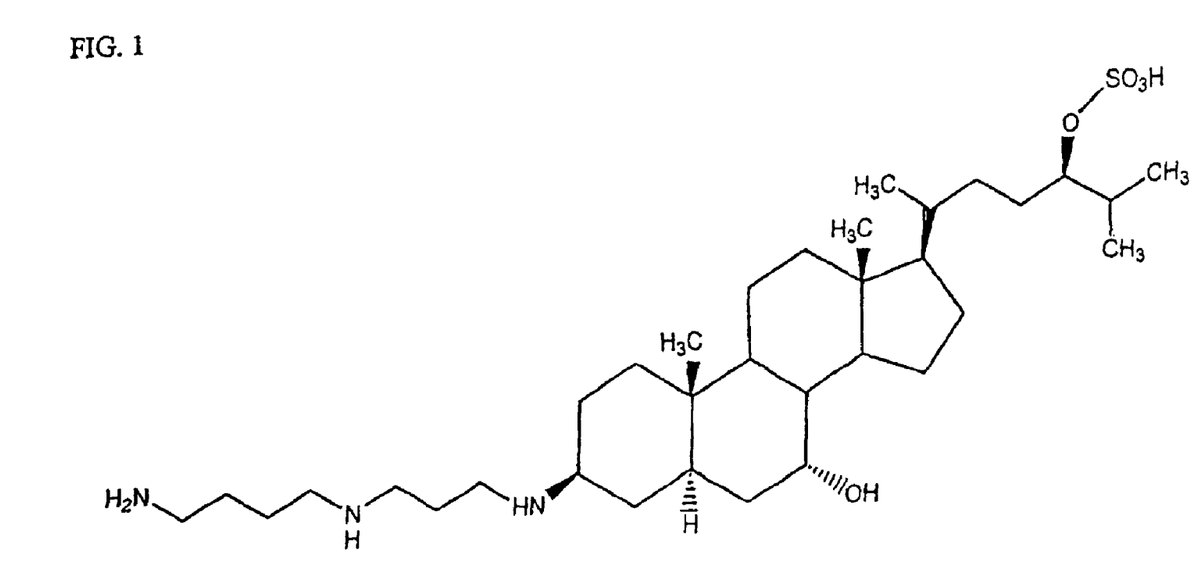
FIG. 1 illustrates the chemical structure of squalamine.

Several aminosterol compositions have been isolated from the liver of the dogfish shark, *Squalus acanthias*. One important aminosterol is squalamine (3β-(N-[3-aminopropyl]-1,4-butanediamine)-7α, 24R-dihydroxy-5α-cholestane 24-sulfate), illustrated FIG. 1. The aminosterol squalamine, which includes a sulfate group at the C-24 position, is the subject of U.S. Pat. No. 5,192,756 which also describes the aminosterol's antibiotic properties.

Since the discovery of squalamine, however, several other interesting properties of this compound have been discovered. For example, as described in U.S. Pat. Nos. 5,733,899 and 5,721,226, squalamine may function as an antiangiogenic agent useful for the treatment of cancers. See U.S. Pat. No. 6,147,060. Additional uses of squalamine such as an agent for inhibiting NHE3 and as an agent for inhibiting endothelial cell growth are disclosed in U.S. Pat. No. 5,792,635.

Methods for synthesizing squalamine have been described. See WO 94/19366 which relates to U.S. patent application. Ser. No. 08/023,347. U.S. Pat. No. 5,792,635 also discloses squalamine isolation and synthesis techniques.

Figure 2:
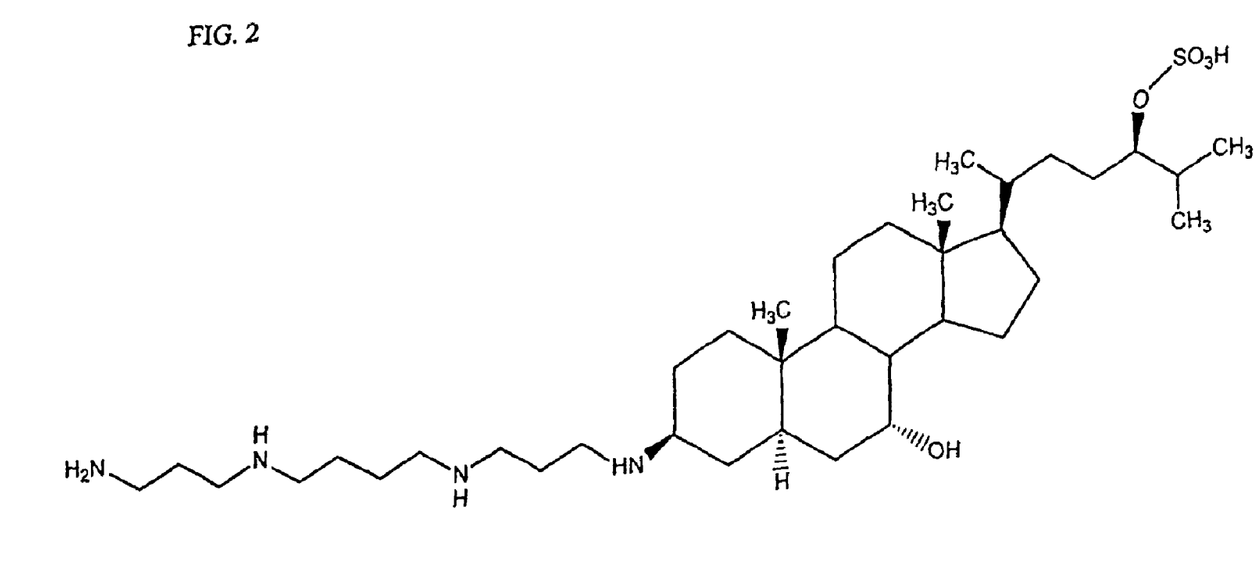
FIG. 2 illustrates the chemical structure of compound 1436.

Stemming from the discovery of squalamine, other aminosterols have been discovered in the dogfish shark liver and have been investigated. One important aminosterol that has been isolated and identified as "compound 1436" or simply "1436" has the structure shown in FIG. 2. This compound has the general molecular formula $C_{37}H_{72}N_4O_5S$ and a calculated molecular weight of 684.53017. Like squalamine, this aminosterol has a sulfate group at the C-24 position.

Compound 1436 previously has been described in U.S. Pat. No. 5,795,885. As further described in this patent, compound 1436 has a variety of interesting properties. For example, compound 1436 inhibits human T-lymphocyte proliferation, as well as the proliferation of a wide variety of other cells and tissues. Additional uses of compound 1436 are disclosed in U.S. Pat. No. 6,143,738. U.S. Pat. Nos. 5,795,885 and 5,847,172 also describe the structure of compound 1436 as well as processes for synthesizing and isolating the compound. For example, compound 1436 can be prepared from a squalamine starting material.

Difficulties have been encountered, however, when attempting to provide a process for synthesizing squalamine or compound 1436 from commercially available starting materials (i.e., not from shark liver isolates). These difficulties include low overall yields of the desired steroid product as well as multiple synthetic steps.

Additional difficulties are encountered in providing a sulfate group at the C-24 position. Particularly, it is difficult to provide the sulfate group at the C-24 position in a highly stereoselective orientation. See, for example, Pechulis, et al., "Synthesis of 24R-Squalamine, an Anti-Infective Steroidal Polyamine," *J. Org. Chem.*, 1995, Vol. 60, pp. 5121–5126; and Moriarty, et al., "Synthesis of Squalamine. A Steroidal Antibiotic from the Shark," *Tetrahedron Letters*, Vol. 35, No. 44, (1994), pp. 8103–8106.

Because of the importance of squalamine, compound 1436, other aminosterols, 24R and 24S-hydroxylated steroids and vitamin-$D_3$ metabolites, there has been considerable interest in preparing stereospecific compounds especially at the C-24 position. As mentioned above, processes for producing squalamine and compound 1436 have been described. However, these processes do not enable large scale production of the desired aminosterol compounds because relatively low yields are realized by these processes.

Processes for stereoselectively producing cerebrosterol, MC 903, and 1α, 24(R)-dihydroxyvitamin $D_3$ have been developed. Koch, et al., "A Stereoselective Synthesis and a Convenient Synthesis of Optically Pure (24R)- and (24S)-24 hydroxycholesterols," *Bulletin de la Société Chimique de France*, 1983, (No. 7–8), Vol. II, pp. 189–194; Calverley, "Synthesis of MC 903, a Biologically Active Vitamin D Metabolite Analogue," *Tetrahedron*, 1987, Vol. 43, No. 20, pp. 4609–4619; and Okamoto, et al. "Asymmetric Isopropylation of Steroidal 24-Aldehydes for the Synthesis of 24(R)-Hydroxycholesterol, *Tetrahedron: Asymmetry*, 1995, Vol. 6, No. 3, pp. 767–778. These processes attempt to reduce 22-ene-24-one and 22-yne-24-one systems in a stereoselective manner. Unfortunately, the processes were not highly stereospecific and often resulted in mixtures of the 24R and 24S which were difficult to separate. Thus these processes were not conducive to large scale synthesis.

Other attempts were also not conducive to large scale synthesis. These processes suffered from being too lengthy or impractical. For example, successful reduction has been achieved of a related 25-ene-24-one system using Noyor's 2,2'-dihydroxy-1,1'-binaphthyl lithium aluminum hydride reagent at −90° C. to give 95:5 selectivity for the 24R-alcohol. Ishiguro, et al. "Stereoselective Introduction of Hydroxy-Groups into the 24-, 25-, and 26-Positions of the Cholesterol Side Chain," *J. C. S. Chem. Comm.*, 1981, pp. 115–117. However, the 25-ene-24-one intermediate material producible in four steps) is less readily accessible than the 22-ene-24-one system (producible in one step). Furthermore, the low temperature required for the chiral reduction also detracts from the commercial practicality of this method.

A large scale stereoselective synthesis has been developed to satisfy the requirements for rapid entry in Phase I clinical trials. Zhang, X., et al., *J. Org. Chem.*, 63, 8599–8603 (1998). However, the synthesis suffered two major drawbacks. First, the synthesis was quite lengthy. Secondly, introduction of a 7α-hydroxyl group proved problematic.

Thus there exists a need in the art for a method of preparing aminosterol compounds such as squalamine, compound 1436 and various homologs that overcome the drawbacks of prior synthetic methods.

SUMMARY OF THE INVENTION

The present invention answers such a need by providing a short and regio- and stereoselective method of preparing aminosterol compounds. According to a method of the invention, regio- and stereoselective oxidation and sulfonation can be achieved with fewer protecting groups and consequently fewer steps.

The invention also provides a method of regioselectively and stereoselectively oxidizing a primary hydroxyl substituent in the presence of a secondary hydroxyl substituent attached to the same fused ring system.

The invention further provides a method of regioselectively sulfonating one secondary hydroxyl substituent over another secondary hydroxyl substituent attached to the same fused ring system.

A method of the invention also provides novel intermediate compounds.

BRIEF DESCRIPTION OF THE DRAWINGS

Advantageous aspects of the invention will be evident from the following detailed description which should be considered in conjunction with the attached drawings, wherein.

DETAILED DESCRIPTION OF THE INVENTION

Microbial hydroxylation has been achieved in steroid chemistry Mahato, S. B., et al., *Steroids*, 62, 332–345 (1997). Despreaux has described the microbial 7α-hydroxylation of 3-ketobisnorcholenol (1, Scheme 1 below) using the species *Botryodiplodia theobromae*. Despreaux, C. W., et al., *Appl. Environ. Microbiol.*, 51, 946–949 (1986); Despreaux et al., U.S. Pat. No. 4,230,625; and Despreaux et al., U.S. Pat. No. 4,301,246. This invention uses steroid compound 2 as a starting material for the synthesis of squalamine, 1436 and homologous aminosterols. A method of the invention introduces the 7-α-hydroxyl group using microbial hydroxylation and proceeds without protection of the 7-hydroxyl group. A general outline of a method of the invention is outlined in Scheme 1 below:

Scheme 1

Aminosterol Compounds

According to a method of the invention, steroid 2 may be converted to aminosterol compounds such as, but not limited to, squalamine, compound 1436 and aminosterol homologs by means of two regioselective reactions without the use of protecting groups. According to the invention, in a fused ring sytem, a primary hydroxyl moiety can be selectively oxidized over a secondary hydroxyl moiety. For example, if the fused ring system has a steroidal structure, as described below, a C-22 primary hydroxyl moiety can be selectively oxidized over a secondary hydroxyl moiety at the C-7 position. Also according to the invention, in a fused ring system, one secondary hydroxyl moiety can be selectively sulfonated over another secondary hydroxyl moiety. For example, if the fused ring system has a steroidal structure, as described below, a C-24 secondary hydroxyl moiety can be selectively sulfonated over a C-7 secondary hydroxyl moiety. According to the invention, relatively high yields (e.g. 77%) as well as regioselectivity and stereoselectivity may be achieved. Some C24 selectivity has been shown in the sulfonation reaction on a spermidinyl-steroidal diol. However, this reaction not only required heating and protection of the C7-OH group, but the yield of the compound was low (10%). Moriarty, R. M., et al., *Tetrahedron Lett.*, 35, 8103–8106 (1994).

An example of the invention provides a short and regioselective method of preparing an aminosterol compound of the general formula I:

(I)

In formula I, $NR_1R_2$ may be any saturated or unsaturated, linear or branched amino group. According to the invention, such an amino group may contain more than one nitrogen. Preferably, in formula I:

$R_1$ and $R_2$ are independently selected from the group consisting of: H, alkyl, alkenyl, alkynyl, $-(CH_2)_n$ $NH-(CH_2)_m-NH_2$, and $-(CH_2)_n-NH-(CH_2)_m-NH-(CH_2)_p-NH_2$;

n is an integer from 1–3;

m is an integer from 1–4; and p is an integer from 1–2.

Most preferably, the compound of formula (I) is squalamine or compound 1436. According to the invention, an amino sterol compound of formula I may be prepared by (a) reacting compound 2:

under conditions sufficient to form compound 3:

(b) reacting compound 3 under conditions sufficient to form compound 4:

(c) reacting compound 4 under conditions sufficient to form compound 5:

(d) reacting compound 5 under conditions sufficient to form compound 7:

(e) reacting compound 7 under conditions sufficient to form compound 8:

(f) reacting compound 8 under conditions sufficient to form compound 9:

(g) reacting compound 9 under conditions sufficient to form compound 10:

9

(h) reacting compound 10 under conditions sufficient to form compound 11:

10

(i) reacting compound 11 under conditions sufficient to form an aminosterol compound of the general formula (I), as described above. Each of the compounds produced by a method of the invention may be isolated and purified using techniques known in the art including, but not limited to, extraction and chromatography. Each of the compounds produced by a method of the invention may be characterized using techniques known in the art such as, for example, mass spectrometry, $^1$H NMR and $^{13}$C NMR.

11

As set forth above, a method according to the invention includes processes for regioselectively oxidizing a C-22-OH group in the presence of a C-7-OH group as well as the regioselective sulfonation of a C-24-OH group in the presence of a C-7-OH group. With respect to steps (a)–(i) of a method of the invention, "under conditions sufficient" may be any synthetic method that achieves the desired transformation without effecting the stereochemistry of the remainder of the molecule. With respect to step (a), compound 2 may be transformed or converted to compound 3 using reduction methods known in the art. Despreaux, C. W., et al., Appl. Environ. Microbiol., 51, 946–949 (1986); Starr, J. E., Editor: C. Djerassi, Holden-Day, Inc., San Francisco, Chapter 7, pgs. 300–307 "Steroid Reaction" (1963). Preferably, reduction is achieved using lithium in ammonia with, preferably, yields of at least about 76%.

Compound 3 may be transformed or converted to compound 4 by any protecting method known in the art, preferably, by ketalization of the carbonyl moiety. Ketalization may be performed utilizing ethylene glycol in chlorotrimethylsilane in good yield. Chan, T. H., et al., Synthesis, 203–205 (1983).

Compound 4 may be transformed or converted to compound 5 by regioselective oxidation of the primary alcohol at the C-22 position, preferably by reaction with bleach in the presence of a catalyst. The bleach may be any bleach, preferably sodium hypochlorite (NaOCl). The catalyst may be any catalyst which in combination with the bleach achieves the regioselective oxidation. Preferably, the catalyst is a TEMPO catalyst (2,2,6,6-tetramethyl-1-piperidinyloxy free radical, commercially available from Aldrich Chemicals, Milwaukee, Wis.). Preferably, conditions are chosen such that yields of about 98% are achieved. Anelli, P. L., et al., Org. Syn., Vol. 69, page 212, "A General Synthetic Method for the Oxidation of Primary Alcohols to Aldehydes: (S)-(+)-2 Methylbutanal".

Compound 5 may be transformed or converted to compound 7 by a carbon-carbon double bond formation reaction (e.g., Wittig reaction, Wadsworth-Emmons reaction, Peterson olefination reaction). Preferably, compound 5 is reacted with Wadsworth-Emmons reagent 6 (Jones, S. R., et al., J. Org. Chem., 63, 3786–3789 (1998)):

6 to afford enone compound 7 efficiently (82%).

Compound 7 may be transformed or converted to compound 8 by reduction of the C-24 carbonyl moiety in good yield. Compound 8 may be transformed or converted to compound 9 by reduction of the C22 double bond. Preferably, reduction was achieved by means of hydrogenation. Compound 9 may be transformed or converted to compound 10 by deprotection of the C3 carbonyl.

Compound 10 may be transformed or converted to compound 11 by regioselective sulfonation of C24 hydroxyl group, preferably, by reacting compound 10 with a very small excess (5%) of sulfur-trioxide complex. Preferably, the diastereomeric excess in the sulfate is about 95% based on the HPLC method.

Lastly, compound 11 may be transformed or converted to the desired aminosterol compound (e.g. squalamine, compound 1436 or homologous compounds) by any means whereby a carbonyl moiety may be converted to an amino group including, but not limited to, reductive amination conditions. Rao, M., et al., J. Nat. Prod. 63, pp. 631–635 (2000); Zhang, X., et al., J. Org. Chem. 63, 8599–8603 (1998); and Weis, A. L., et al., Tetrahedron Lett., 40, 4863–4864 (1999).

An example of a preferred method of preparing aminosterol compound squalamine is illustrated in Scheme 2 below:

Scheme 2

-continued

Squalamine

The invention also provides a method of regioselectively oxidizing a primary hydroxyl substituent in the presence of a secondary hydroxyl substituent attached to the same fused ring base. According to this embodiment of the invention, a fused ring base to which both a primary hydroxyl substituent and a secondary hydroxyl substituent are attached is reacted with bleach in the presence of a catalyst whereby solely the primary hydroxyl substituent is oxidized to an aldehyde. According to the invention a fused ring base is any compound containing at least two saturated and/or unsaturated ring systems which share at least two carbon atoms. According to the invention, the fused ring base may also contain appropriate substituents (e.g. alkyl groups, hydroxyl groups, amino groups, etc.) or unsaturations (e.g. double bonds, triple bonds, carbonyl groups). An appropriate substituent or unsaturation is one that would not adversely effect the desired transformation or conversion, as described below. Preferably, the fused ring base is a steroid ring system having the following general formula:

where R is a linear or branched, substituted or unsubstituted, saturated or unsaturated alkyl group. Preferably, the fused ring base has one of the following structures:

and

The bleach and the catalyst are each as described herein.

The invention also provides for a method of regioselectively sulfonating one secondary hydroxyl substituent in the presence of another secondary hydroxyl substituent attached to the same fused ring base. The fused ring base is as described above except that the preferred fused ring base has the following structure:

According to this embodiment of the invention, a fused ring base to which two secondary hydroxyl substituents are attached is reacted with sulfur-trioxide pyridine complex (commercially available from Aldrich Chemical, Milwaukee, Wis.):

The methods of the invention achieve regioselectivity of one hydroxyl moiety in the presence of another unprotected hydroxyl moiety. The methods of the invention achieve regioselectivity of at least about 9:1 excess of the desired hydroxylated or sulfonated compound. Preferably, selectivity of greater than about 19:1 is achieved, and most preferably, greater than about 33:1 selectivity is achieved.

The methods of the invention as described above may be used to produce a hydroxylated intermediate that can be further modified, as described above, to produce the desired final product. The methods of the invention produce regiospecific intermediates that can be further modified to synthesize squalamine, compound 1436, other useful aminosterols or steroids having stereospecific groups (e.g., C-24 sulfate groups in an R orientation for, squalamine and compound 1436). Such intermediates include, but are not limited to, compounds 3–10 as illustrated in Scheme 2 above.

The methods of the invention will now be described in specific examples. However, the following examples serve merely to illustrate the invention and are not meant to limit the invention in any manner.

EXAMPLES

Regioselective and Stereoselective Synthesis of a Precursor for Squalamine, Compound 1436 or Homologous Aminosterols General. The $^1$H and $^{13}$CNMR spectra were generated at 400 and 100 MHz, utilizing 7.28 and 77.0 (CDCl$_3$) ppm as the references respectively. Elemental analyses were performed at Oneida Research Services, Inc., Whitesboro, N.Y. Fast Atom Bombardment mass spectral analysis was carried out at M-Scan Inc., West Chester, Pa.

Example 1

Preparation of (5-α-, 7-α-)-3-Ketobisnorcholan-7, 22-diol (3)

Liquid ammonia (125 mL) was treated with tetrahydrofuran (15 mL) and lithium (300 mg, 43 mmol) and stirred for 30 min. Then a solution of 2 (Despreaux, C. W., et al., *Appl. Environ. Microbiol.*, 51, 946–949 (1986)) (352 mg, 1.20 mmol) in tetrahydrofuran (20 mL) and ethanol (0.4 mL) was added. The reaction mixture was stirred for 40 min and then 20 g of ammonium chloride was added. The solvent was evaporated under nitrogen and the residue was treated with water (200 mL) and extracted with ethyl acetate (3×75 mL). The organic phase was washed with brine, dried over sodium sulfate, filtered, and evaporated. Purification of the resulting solid by flash chromatography on silica gel (hexane-ethyl acetate-methanol 10:10:1) afforded pure 3 (251 mg, 71%, mp 221–223° C., MW 348.53); $^1$H NMR (CDCl$_3$): δ3.86 (br s, 1H), 3.65–3.62 (m, 1H), 3.39–3.36 (m, 1H), 2.34–1.18 (m, 23H), 1.05 (d, J=6.6 Hz, 3H), 1.01 (s, 3H), 0.71 (s, 3H); $^{13}$C NMR (CDCl$_3$): δ 67.9, 67.4, 52.4, 50.2, 45.2, 44.1, 42.7, 39.5, 39.2, 39.0, 38.7, 38.1, 36.5, 35.6, 27.7, 23.7, 21.2, 16.7, 11.9, 10.4; MS (+FAB): 349 ([M+I]$^+$, 100), 331 (52); Anal. Calcd for C$_{22}$H$_{36}$O$_3$: C, 75.82; H, 10.41. Found: C, 75.71; H, 10.19.

Example 2

(5-α-, 7-α-)-3-Dioxolane Bisnorcholan-7,22-diol (4)

To a mixture of steroid 3 (101 g, 0.290 mol) of Example 1 and anhydrous ethylene glycol (800 mL) was added chlorotrinethylsilane (200 mL, 1.58 mol) over 60 min at room temperature under nitrogen. The reaction mixture was stirred at room temperature for 19 h. The mixture was poured slowly into saturated sodium bicarbonate solution (1 L) and extracted with dichioromethane (3×500 mL). The organic layer was washed with brine (3×150 mL) and dried over sodium sulfate (20 g). After filtration and evaporation, the product was recrystallized from ethyl acetate in hexane (800 mL). The solid was filtered and washed with hexane (150 mL) to afford 4 (96.14 g, 84%, mp 173–175° C., MW 392.58); $^1$H NMR (CDCl$_3$): δ3.93 (s, 4H), 3.83 (br s, 1H), 3.65 (d of d, J=10.4 and 3.1 Hz, 1H), 3.36 (d of d, J=10.4 and 7.1 Hz, 1H), 2.0–1.8 (m, 3H), 2.7–1.1 (m, 21H), 1.05 (d, J=6.6 Hz, 3H), 0.82 (s, 3H), 0.69 (s, 3H); $^{13}$C NMR (CDCl$_3$): δ 109.2, 67.8, 64.1, 52.4, 50.3, 45.6, 42.7, 39.5, 39.3, 38.8, 37.4, 36.2, 36.1, 35.7, 35.5, 31.2, 27.7, 23.7, 20.9, 16.7, 11.9, 10.3; MS (+FAB): 394 ([M+I]$^+$, 100); Anal. Calcd for C$^{24}$H$^{40}$O4: C, 73.43; H, 10.27. Found: C, 73.15; H, 10.15. This reaction was accomplished at 10% concentration of substrate, which allows for efficient scale-up of the procedure.

Example 3

Preparation of (5-α, 7-α-)-3-Dioxolane-7-hydroxy Bisnorcholan-22-al, (5)

To a solution of 4 (100 g, 255 mmol) of Example 2 in methylene chloride (1,200 mL) was added potassium bromide (3.19 g, 26.8 mmol) and sodium bicarbonate (10.97 g, 130 mmol) dissolved in water (120 mL). The cooled (0° C. reaction mixture was treated with TEMPO (1.20 g, 7.7 mmol) and 10–13%,sodium hypochlorite (170 mL, 275–358 mmol). After stirring (magnetic) for 2 h at 0° C., the reaction mixture was treated with sodium thiosulfate (20 g, 126 mmol) in water (220 mL). The organic phase was separated, washed with brine (3×70 mL), dried over sodium sulfate (30 g), filtered, and concentrated in vacuo for 18 h at room temperature to afford 5 (99.5 g, 98%, MW 390.57, FW 397.77); $^1$H NMR (CDCl$_3$): δ9.57 (d, J=3.4 Hz, 1H), 3.95 (s, 4H), 3.83 (br s, 1H), 3.76 (m, 1H), 2.3 5 (m, 1H), 2.0–1.2 (m, 21 H), 1.13 (d, J=6.8 Hz, 3H), 0.83 (s, 3H), 0.72 (s, 3H); $^{13}$C NMR (CDCl$_3$): δ 204.9, 109.0, 67.6, 64.0, 50.8, 49.7, 49.3, 45.4, 43.0, 39.3, 39.0, 37.3, 36.2, 35.9, 35.6, 35.4, 31.0, 26.8, 23.8, 20.7, 13.3, 12.1, 10.2; MS (+FAB): 391 ([M+I]$^+$, 100); Anal. Calcd for C$_{24}$H$_{38}$0.4-H$_2$O: C, 72.47; H, 9.83. Found: C, 72.49; H, 9.77.

Example 4

Preparation of (5-α-, 7-α-)-3-Dioxolane-7-hydroxy Cholest-23-en-24-one (7)

A mixture of 97% sodium t-butoxide (37 g, 373 mmol) and anhydrous tetrahydrofuran (400 mL) was stirred for 10 min under nitrogen and then a solution of 6 (94 g, 423 mmol, see Scheme 2 above) in tetrahydrofuran (150 mL) was added in one portion. The mixture initially warmed to 41° C., but returned to 24° C. while stirring (45 min). Then a solution of 5 (99.48 g, 250 mmol) of Example 3 in tetrahydrofuran (400 mL) was added over 60 min. The reaction mixture was stirred overnight at room temperature (18 h) and then water was added (30 mL). The reaction mixture was concentrated in vacuo and treated with cyclohexane (1200 mL), toluene (600 mL) and water (160 mL). The organic layer was separated, washed with brine (3×100 mL) and water (160 mL), dried over sodium sulfate (30 g), filtered, and evaporated to yield a solid. The crude solid was recrystallized from ethyl acetate in cyclohexane and dried in vacuo at 50° C. for 5 h to yield 7 (94.64 g, 82%, mp 177–178° C., MW 458.69); $^1$H NMR (CDCl$_3$): δ 6.72 (d of d, J=15.7 and 9.0 Hz, 1H), 6.07 (d, J=15.7 Hz, 1H), 3.94 (s, 4H), 3.83 (br s, 1H), 2.85 (hept, J=6.9 Hz, 1H), 2.29 (m, 1H), 2.0–1.1 (m, 22 H), 1.11 (m, 9H) 0.83 (s, 3H), 0.71 (s, 3H); $^{13}$C NMR (CDCl$_3$): δ204.5, 152.4, 126.2, 109.1, 67.8, 64.1, 54.9, 50.4, 45.6, 43.0, 40.0, 39,5, 39.3, 38.1, 37.4, 36.3, 36.1, 35.7, 31.2, 28.1, 23.6, 20.9, 19.3, 18.6, 18.4, 12.1, 10.3; MS (+FAB): 459 ([M+1]$^+$, 92), 99 (100); Anal. Calcd for C$_{29}$H$_{46}$O$_4$: C, 75.94; H, 10.11. Found: C, 75.57; H, 9.87.

Example 5

Preparation of (5-α-, 7-α-, 24S-)-7, 24-Dihydroxy-3-dioxolane Cholest-23-ene (8)

A dried and nitrogen blanketed reactor was charged with 1 M (R)-MeCBS reagent in toluene (20 mL, 20 mmol) and 1 M borane-tetrahydrofuran complex in tetrahydrofuran (25 mL, 25 mmol) and stirred for 2 h at room temperature. The reaction mixture was cooled (−15 to −28° C.), treated with steroid 7 (9.16 g, 20 mmol) of Example 4 in tetrahydrofuran (150 mL), and stirred for 2 hr (−20 to −28° C.). The reaction mixture was treated with methanol (25 mL) with stirring for 18 hr at room temperature, and then repeatedly evaporated by distillation and treated with methanol (4×30 mL) to exchange solvents. Finally methanol (70 mL) was added and the reaction mixture was brought to reflux, cooled in the freezer (no crystals formed), and concentrated in vacuo. Recrystallization from acetonitrile (100 mL), filtration, and evaporation at 50–60° C. for 7 hr afforded crystals of 8 (7.43 g, 80%, mp 121–125 ° C., MW 460.70, FW 464.3 1); $^1$H NMR (CDCl$_3$): δ 5.5–5.3 (m, 2H), 3.94 (s, 4H), 3.82 (br s, 1H), 3.75 (in, 1H), 2.2–1.1 (m, 25H), 1.05 (d, J=6.6 Hz, 3H), 0.94 (d, J=6.7 Hz, 3H), 0.88 (d, J=6.8 Hz, 3H), 0.83 (s, 3H), 0.70 (s, 3H); $^{13}$C NMR (CDCl$_3$): δ139.5, 128.6, 109.2, 78.5, 67.8, 64.1, 55.5, 50.6, 45.6, 42.6, 40.0, 39.5, 39.4, 37.5, 36.2, 36.1, 35.7, 35.6, 33.9, 31.2, 28.7, 23.6, 20.9, 20.4, 18.3, 18.1, 12.0, 10.3; MS (+FAB): 462 ([M+I]$^+$, 100); Anal. Calcd for $C_{29}H_{48}O_4$-0.2H$_2$O: C, 75.02; H, 10.51. Found: C, 75.00; H, 10.48.

Example 6

Preparation of (5-α-, 7-α-, 24R-)-7, 24-Dihydroxy-3-dioxolane Cholestane (9)

Steroid 8 (10.0 g, 21.5 mmol) of Example 5, toluene (170 mL), triethylamine (1 mL), and 10% platinum on carbon (0.5 g) were combined under 50 psi of hydrogen in a Parr apparatus (19 h). The reaction mixture was filtered through Celite (10 g), washed with chloroform and ethyl acetate (10 mL total), and concentrated in vacuo to afford a solid, which was recrystallized from ethyl acetate in hexane (180 mL). The solid was filtered and concentrated at 50–60° C. under vacuum for 7 h to afford pure 9 (9.24 g, 92%, mp 161–163° C., MW 462.72, FW 466.32); $^1$H NMR (CDCl$_3$): δ 3.95 (s, 4), 3.84 (br s, 1H), 3.33 (br s, 1H), 2.0–1.1 (m, 29H), 0.93 (m, 9H), 0.83 (s, 3H), 0.67 (s, 3H); $^{13}$C NMR (CDCl$_3$): δ 109.2, 77.0, 67.8, 64.1, 55.9, 50.5, 45.5, 42.6, 39.5, 37.4, 36.2, 36.1, 35.7, 35.5, 33.5, 32.0, 31.2, 30.5, 28.2, 23.6, 20.9, 18.8, 18.6, 17.2, 11.8, 10.3; MS (+FAB): 463 ([M+I]+, 100)$^+$, Anal. Calcd for $C_{29}H_{50}O_4$-0.2H$_2$O: C, 74.70; H, 10.89. Found: C, 74.48; H, 10.49.

Example 7

Preparation of (5-α-, 7α-, 24R-)-7, $^2$4-Dihydroxy-3-ketocholestane (10)

Steroid 9 (2.03 g, 4.35 mmol) of Example 6, p-toluenesulfonic acid (200 mg), water (1 mL), and acetone (100 mL) were combined with stirring for 4 h. The reaction mixture was concentrated in vacuo and treated with dichloromethane (100 mL) and saturated sodium bicarbonate solution (50 mL). The organic layer was removed, washed with brine (3×25 mL), dried over sodium sulfate (10 g), filtered, and evaporated at 50–60° C. The solid was recrystallized from ethyl acetate in hexane (50 mL), filtered, washed with hexane, and dried in vacuo at 50–60° C. for 7 hr to afford 10 (1.63 g, 89%, mp 151–153 C, MW 418.67); $^1$H NMR (CDCl$_3$): δ 3.88 (br s, 1H), 3.33 (br s, 1H), 2.5–1.1 (m, 29H), 1.02 (s, 3H), 0.94 (m, 9H), 0.71 (s, 3H); $^{13}$C NMR (CDCl$_3$): δ 212.0, 76.9, 67.3, 56.1, 50.3, 45.1, 44.1, 42.6, 39.4, 39.0, 38.1, 38.0, 36.6, 35.8, 35.6, 33.6, 32.1, 30.6, 28.2, 23.6, 21.1, 18.9, 18.6, 17.3, 11.8, 10.4; MS (+FAB): 419 ([M+I]$^+$, 100); Anal. Calcd for $C_{27}H_{46}O_3$: C, 77.46; H, 11.07. Found: C, 77.25; H, 11.04.

Example 8

Preparation of Potassium salt of (5-α-7-α-, 24R-)-7-Hydroxy-3-ketocholestan-24-yl Sulfate (11)

A dried and nitrogen blanketed flask was treated with compound 10 (2.09 g, 5.0 mmol) of Example 7 dissolved in anhydrous pyridine (30 mL). Sulfur trioxide pyridine complex (836 mg, 5.25 mmol, 1.05 equiv.) dissolved in pyridine (20 mL) was added to the reaction mixture, which was stirred for 4 h at room temperature. Water was added (10 mL) and the pyridine was removed by concentration in vacuo at 40° C. The residue was treated with ethyl acetate (50 mL) and potassium chloride (1.12 g, 15 mmol) dissolved in water with stirring for 1.5 h. The potassium salt of 11 was collected on Celite (3 g) by filtration, washed with ethyl acetate (50 mL) and water (10 mL), and dissolved in 1 N potassium hydroxide in 15 methanol (10mL, 10 mmol) and methanol (100 mL). The methanol was removed in vacuo to dryness and the solid was washed with water (30 mL), filtered, and dried in vacuo at room temperature for 20 hr to afford 11 (2.10 g, 77%, MW 536.82, FW 544); $^1$H and $^{13}$C NMR were identical to published spectra. HPLC analysis by the method described previously (Zhang, X., et al., *J. Org. Chem.*, 63, 8599–8603 (1998)) indicated a diastereomeric excess of 95%.

Example 9

Preparation of Compound 1436

A clear colorless solution of compound 11 (16 mg, 0.032 mmol) and spermine (20 mg, 0.1 mmol, commercially available from Aldrich) in anhydrous methanol (3 ml) was stirred at room temperature under nitrogen for 12 hours, cooled to −78° C., and treated dropwise with sodium borohydride (1 pellet, 0.4 g, 10 mmol) in methanol (10 ml). This reaction mixture was stirred for 3 hours, treated with a mixture of water and methanol (10 ml each), warmed to room temperature, and then treated with 0.78% trifluoroacetic acid (TFA) solution until its pH reached the range of 4–5. The resulting mixture was filtered through a thin pad of Celite®, and the Celite® was washed with methanol and water (100 ml). Celite® is SiO$_2$ that is commercially available from Aldrich. The combined acidic washes were concentrated in vacuo at room temperature and then freeze-dried overnight to give a white solid. The Celite® cake was then washed with isopropyl amine/methanol/water (140 ml of 1:3:3), and the basic portion was evaporated to reduce its volume. This material was freeze-dried overnight to give a light brown solid. Both washes contained compound 1436, so they were combined and acidified to a pH of 3 with 0.78% TFA, filtered, and loaded onto a small HPLC column (1 cm diameter, see below). The reaction product was compound 1436 (12.2 mg, 36%): $^1$H NMR (400 MHz, D$_2$O): δ 4.14 (m, 11), 3.83 (m, 1H), 3.2–3.0 (m, 13H), 2.1–1.0 (m, 35H), 0.92 (m, 9H), 0.82 (s, 3H), 0.67 (s, 3H); $^{13}$C NMR (400 MHz, D$_2$O): δ87.2, 68.0, 57.9, 56.0, 50.5, 47.4, 45.6, 44.9, 42.8, 41.9, 39.7, 37.5, 36.9, 36.7, 36.0, 35.8, 31.5, 31.1, 30.6, 28.3, 27.1, 24.8, 24.1, 23.6, 23.4, 23.1, 21.4, 19.2, 17.7, 12.1, 11.2; MS (−LD): 684 (M−1); Anal. Calcd. for $C_{37}H_{72}N_4O_5S$-3TFA-2H$_2$O: C, 48.58; H, 7.49; F, 16.08; N, 5.27; S, 3.02. Found: C, 48.49; H, 7.40; F, 16.16; N, 5.31; S, 3.05.

Example 10

Purification of Compound 1436 by HPLC

The crude material of Example 9 was dissolved in water (50 ml), cooled in an ice bath, and acidified with 1.5% TFA in water until its pH was 3. Initially, it was observed that one obtains a suspension as the pH drops, and then a solution is obtained at lower pH. This solution was loaded onto a Rainin reverse phase HPLC system (2.14 cm diameter, C18, 100 Å, 8 μm) and elited with A (water with 0.1% TFA) and B (acetonitrile with 0.1% TFA). The HPLC program was as follows: 10 min (0–10% B), 60 min (10–45% B), 10 min (45–80% B), 10 min (80% B). Pure product eluted in the 33 to 55 minute fractions, as determined by TLC ($R_f$: 0.1–0.2 in 6/3/1 $CH_2Cl_2$/MeOH/$NH_4OH$)(should evaporate plates under vacuum before eluting, and observe with ninhydrin stain after eluting), which was lyophilized to produce 1.20 grams of compound 1436 as a white powder (70%); $C_{37}H_{72}N_4O_5S$-3TFA-2.5$H_2O$, FW 1072.18).

Example 11

Preparation of Squalamine

Squalamine was prepared by reacting the potassium salt of compound 11 (0.5 equivalents) of Example 8 with $H_2N$($CH_2$)$_3$NH($CH_2$)$_4$$N_3$.2HCl (1 equivalent) in NaOMe (2 equiv) and methanol at room temperature for 24 hours and then at −78° C. with $NaBH_4$ followed by treatment with $H_2$, RaNi, RP-HPLC, 69% based on the potassium salt of compound 11. See Weis et al., Tetrahedron Letters, 40, 4863–4864 (1999).

In describing the invention, applicant has stated certain theories in an effort to disclose how and why the invention works in the manner in which it works. These theories are set forth for informational purposes only. Applicants do not wish to be bound by any specific theory of operation.

While the invention has been described in terms of various specific preferred embodiments and specific examples, those skilled in the art will recognize that various changes and modifications can be made without departing from the spirit and scope of the invention, as defined in the appended claims.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference in their entirety.

What is claimed:

1. A compound with the following structure:

2. A compound with the following structure:

3. A compound with the following structure:

4. A compound with the following structure:

* * * * *